(12) United States Patent
Lee

(10) Patent No.: US 11,071,951 B2
(45) Date of Patent: Jul. 27, 2021

(54) CENTRIFUGAL GRADIENT DIALYSATE DUAL-CHAMBER HEMODIAFILTRATOR

(71) Applicant: Choon Kee Lee, Denver, CO (US)

(72) Inventor: Choon Kee Lee, Denver, CO (US)

( * ) Notice: Subject to any disclaimer, the term of this patent is extended or adjusted under 35 U.S.C. 154(b) by 106 days.

(21) Appl. No.: 16/587,012

(22) Filed: Sep. 29, 2019

(65) Prior Publication Data

US 2021/0094002 A1   Apr. 1, 2021

(51) Int. Cl.
    *B01D 63/16* (2006.01)
    *B01D 63/02* (2006.01)
    *A61M 1/34* (2006.01)
    *A61M 1/36* (2006.01)
    *A61M 1/16* (2006.01)
    *B01D 61/28* (2006.01)

(52) U.S. Cl.
    CPC ........... *B01D 63/16* (2013.01); *A61M 1/1623* (2014.02); *A61M 1/3413* (2013.01); *A61M 1/3693* (2013.01); *B01D 61/28* (2013.01); *B01D 63/02* (2013.01); *B01D 2313/08* (2013.01); *B01D 2313/20* (2013.01)

(58) Field of Classification Search
    CPC .... B01D 63/02; B01D 63/16; B01D 2313/08; B01D 2313/20; B01D 61/28; A61M 1/3413; A61M 1/3693; A61M 1/1623
    See application file for complete search history.

(56) References Cited

U.S. PATENT DOCUMENTS

| | | | |
|---|---|---|---|
| 3,422,008 A | 1/1969 | McLain | |
| 3,536,611 A | 10/1970 | De Filippi et al. | |
| 3,616,928 A | 11/1971 | Rosenblatt | |
| 4,002,567 A | 1/1977 | Konno et al. | |
| 4,451,369 A | 5/1984 | Sekino et al. | |
| 4,666,469 A | 5/1987 | Krueger et al. | |
| 4,758,341 A | 7/1988 | Banner | |
| 4,861,485 A * | 8/1989 | Fecondini | A61M 1/3413 210/641 |
| 5,700,372 A * | 12/1997 | Takesawa | A61M 1/342 210/321.6 |
| 9,186,629 B2 | 11/2015 | Mahley et al. | |
| 2002/0053540 A1* | 5/2002 | Collins | B01D 61/28 210/321.8 |
| 2010/0170850 A1 | 7/2010 | Heilmann et al. | |
| 2012/0234746 A1* | 9/2012 | Howard | B01D 65/00 210/321.89 |
| 2020/0384180 A1* | 12/2020 | Lee | B01D 63/02 |

FOREIGN PATENT DOCUMENTS

| | | |
|---|---|---|
| JP | 0464737 B1 | 12/1994 |
| WO | 2014202710 A1 | 12/2014 |
| WO | 2018060510 A2 | 5/2018 |

* cited by examiner

*Primary Examiner* — John Kim

(57) ABSTRACT

The present invention provides a hemodiafiltrator comprising two compartmentalized dialysate chambers coaxially arranged in tandem. A single packed bundle of hollow fibers for blood flow is enclosed coaxially along a longitudinal axis inside the dual dialysate chambers. A configuration of a tandem arrangement of the dual dialysate chambers at least comprises a first dialysate chamber for an acidic dialysate with a varying level of urea and a second compartmentalized dialysate chamber for a basic dialysate with no urea but with a level of ammonia up to a level detected in normal human blood.

18 Claims, 9 Drawing Sheets

CENTRIFUGAL GRADIENT DIALYSATE DUAL-CHAMBER HEMODIAFILTRATOR

TECHNICAL FIELD

The present invention relates generally to the field of blood dialysis. More specifically, the present invention provides a hemodiafiltrator for clinical hemodiafiltration for patients in renal failure.

BACKGROUND OF THE INVENTION

Modern hemodialysis including hemodiafiltration has been advanced to a point that a majority of uremic toxins of small water-soluble molecules (<0.5 kD) and a number of toxins of middle molecules (0.5-60 kD) can be readily removed from blood of uremic patients. However, about a quarter of all the uremic toxins are known to be protein bound molecules, and so far there has not been a hemodialysis (including hemodiafiltration) device or a technology effectively eliminating these protein bound uremic toxins from the blood for clinical use. Recent discoveries and understanding of pathophysiological relationship between the protein bound uremic toxins and cardiovascular morbidity and mortality highlight an urgent need to develop a new technology that would allow efficient and therapeutically effective removal of the protein bound uremic toxins from the blood.

A number of studies revealed that the protein bound uremic toxins are removed by active secretory processes at proximal convoluted renal tubules. However, mechanisms of transporting the protein bound uremic toxins from the blood to a tissue side of the proximal convoluted tubular epithelial cells are not known and elusive. At least for our understanding of an early process of freeing the protein bound uremic toxins from binding proteins, a key process should be that electrostatic charges of protein residues binding the protein bound uremic toxins should change to a point that there come unfolding of a tertiary structure of the binding proteins, and neutralization of non-covalent and covalent binding forces of the protein residues. This critical first step, in fact, occurs in glomeruli through which the blood loses a major portion of bicarbonate by passive filtration averaging about 4200 mmol/day for adults with normal renal function, thereby significantly lowering a pH of the blood in efferent blood vessels coming out from glomerular vascular complexes until the bicarbonate, reabsorbed and newly made in proximal and distal convoluted tubules, respectively, is reclaimed back to the blood that is existing from a network of efferent peritubular capillaries. The peritubular capillaries are closely intertwined with the proximal and distal convoluted tubules in the cortical and medullary portions of the renal tissue. It stands to reason that the critical first step of unbinding of the protein bound uremic toxins from the binding proteins to become "freed protein bound uremic toxins" occurs in an acidified blood over a segment of the peritubular capillaries by the loss of the bicarbonate from the blood through the glomeruli since an average iso-electric point (pI) of blood proteins is known to around 6.8 including serum albumin.

Unless the protein bound uremic toxins are released free from the binding proteins and removable (dialysable; diafiltrarable), it would be difficult for currently available hemodialysis (including hemodiafiltration) devices and technologies to successfully remove the protein bound uremic toxins from the blood of the uremic patients. Based on the acidification of the blood in the efferent peritubular capillaries existing from the glomeruli following glomerular filtration described above, it can be accomplished first by acidifying the blood in a hemodialysis (including hemodiafiltration) system so as to free the protein bound uremic toxins from the binding proteins, secondly by removing the freed protein bound uremic toxins from the blood by the hemodialysis and the hemodiafiltration, and thirdly by normalizing a pH of the acidified blood before it returns to the patient. In laboratories over many decades, this particular method of separating protein bound molecules from the binding protein has been well known as "iso-electric focusing". Since dialysate is produced by a proportioning system combining bicarbonate as a base (alkaline) source with lactate, citric acid, or glacial acetic acid as an acid source, a range of dialysate solutions, with each dialysate solution having a different pH from other dialysate solutions, can be straightforwardly produced by programming the proportioning system so as to vary concentrations of each component in a final mixture of a particular dialysate solution.

The acidification of the blood from the human body drawn into a packed bundle of hollow fibers of hemodialyzer or hemodiafiltrator so as to lower the pH of the blood to a preset level such as 6.0 can be accomplished by a first dialysate solution having a higher concentration of the acid source than a usual proportioning concentration ratio of "1 of acid:1.72 of base:42.28 of water" for the current hemodialysis. Similarly, normalization of the pH of the acidified blood by the acidification in the hollow fibers back to 7.35-7.45 can be achieved by a second dialysate solution having a higher concentration of the base source than the usual proportioning concentration ratio. The second dialysate solution is configured to neutralize an excess H+ of the blood donated by the first dialysate solution, before the blood returns to the human body. It is advantageous to sequence the acidification of the blood and the neutralization of the pH of the acidified blood in tandem over a single unit of the packed bundle of the hollow fibers in order to reduce an overall shear stress imposed on blood cells going through the hollow fibers. Furthermore, it may be necessary to forcefully flush out the freed protein bound uremic toxins from the acidified blood by the hemodialysis or the hemodiafiltration since a majority of charged moieties of the freed protein bound uremic toxins may be altered for their electrostatic state in the acidifying dialysate to a point that water solubility of the freed protein bound uremic toxins may be adversely affected. One issue of the forceful removal of the freed protein bound uremic toxins by the hemodialysis and the hemodiafiltration would be that a significant portion of normal proteins of the acidified blood would be in an unfolded configuration, thereby vulnerable to a shear stress of the dialysate going through the normal proteins. It is yet unknown as to whether the shear stress by the dialysate to the normal proteins in the unfolded configuration would impact on a range of function of the normal proteins following the normalization of the pH of the acidified blood. This unique issue may be minimized by limiting a volume of the acidified blood to be exposed to the shear stress of the dialysate for the forceful removal of the freed protein bound uremic toxins. This can be accomplished by compartmentalizing and minimizing a portion of a hemodialyzer (including hemodiafiltrator) for the forceful removal of the freed protein bound uremic toxins, separating from a portion for the acidification of the blood and from a portion for the normalization of the pH of the acidified blood.

A second factor for consideration of binding and unbinding of protein bound uremic toxins to and from, respectively, blood proteins is presence of urea. A high concentration of urea is well known for its potential for denaturing nascent proteins (unfolding a tertiary structure of proteins) by hydrogen bonding mechanisms and non-hydrogen bonding mechanisms. Although there is no known level of blood urea as a threshold point for an unfolded configuration of the blood proteins, it stands to reason that patients with chronic renal failure having higher concentrations of blood urea than that of normal person have an increase in degree and concentration of the blood proteins in the unfolded configuration which favor release of the protein bound uremic toxins from binding sites of the blood proteins to a blood compartment in a form of freed protein bound uremic toxins. Hemodialysis and hemodiafiltration which are highly effective in removing small water soluble molecules including urea reduces the urea much more efficiently than removing middle molecules to which protein bound uremic toxins belong. Consequently, in an early phase of hemodialysis and hemodiafiltration, the blood urea is removed rapidly and concentration of the blood urea decreases substantially before the freed protein bound uremic toxins can be removed from the blood. Rapid reduction in the concentration of the blood urea by the hemodialysis and hemodiafiltration before removal of the freed protein bound uremic toxins from the blood promotes refolding of the blood proteins from the unfolded configuration. The blood proteins in the refolded configuration then bind the freed protein bound uremic toxins in the blood, resulting in no net changes in concentration of "bound fraction+freed fraction" of the protein bound uremic toxins. In between sessions of the hemodialysis and the hemodiafiltration, the concentration of the blood urea inevitably increases in the patients with the chronic renal failure, thereby promoting the unfolded configuration of the blood proteins, which then results in release of the protein bound uremic toxins from the binding sites of the blood proteins into the blood compartment of the freed protein bound uremic toxins. If an abnormally high concentration of the urea is maintained without change in a portion of a hemodialyzer and a hemodiafiltrator during the hemodialysis and the hemodiafiltration, respectively, the blood proteins in the unfolded configuration would not be able to bind back the freed protein bound uremic toxins which then can be removed by ongoing hemodialysis and the hemodiafiltration.

A third factor to consider for folding and unfolding of the tertiary structure of the proteins having binding sites for the protein bound uremic toxins is blood ammonia that is newly synthesized by and transported from medullary tissues of kidney to peritubular capillaries and renal veins. Although we lack a full understanding on physiologic and biochemical contribution of blood ammonia to homeostasis of renal function, ammonia has been well known for its vital contribution to production of bicarbonate in the medullary tissues of the kidney. Unlike breath ammonia level, blood ammonia level has been shown to be remarkably steady even in patients with fully blown chronic renal failure requiring dialysis, without much difference from that of normal people. High levels of blood ammonia are a well known detrimental factor for the human body, and the blood ammonia is known to be metabolized by liver so as to maintain the steady state of the blood ammonia level. In one study, an average blood ammonia level of the patients with chronic renal failure was approximately 20 micro-mol/L, whereas the level in normal individuals was 25 micro-mol/L without statistical differences. It is well known that about 50% of newly synthesized ammonia from the medullary tissues of the kidney is transported into the blood via the peritubular capillaries, and the other half is used to maintain acid-base homeostasis by generation of bicarbonate and as secretable ammonia in urine especially in a setting of metabolic acidosis. Furthermore, the blood level of ammonia was shown to increase upon the hemodialysis in the study from 21 micro-mol/L to 23 micro-mol/L. All of these indicate that there is a feedback loop system in the human body comprising the liver and kidneys tightly regulating the level of blood ammonia, and that there should be a physiologic role for transported ammonia across the peritubular capillaries from the medullary tissues to the blood since both transportation process of ammonia and metabolism of the transported ammonia by the liver require an input of energy. As of now, we do not have good understanding on the physiologic role of the transported ammonia, especially on the folding and unfolding of the tertiary structure of the blood proteins in the peritubular capillaries, except that ammonia has a molecular dipole moment of 1.47 D indicating presence of charged polarity. Water has the molecular dipole moment of 1.85 D, and is known to form a hydration layer on a surface of proteins and maintain solubility of the proteins.

In laboratory settings, presence of salts such as $(NH_4)_2SO_4$ above a concentration of 0.15 M~0.5M increases surface tension of the water molecules, promoting precipitation of the proteins due to increased hydrophobic interaction between the water molecules and the proteins (salting-out). Below the concentration of 0.15 M~0.5M, the tertiary structure of the proteins begins unfolding (salting-in), thereby increasing solubility of the proteins. According to Hofmeister series, $(NH_4)_3PO_4$ is more effective than $(NH_4)_2SO_4$ for solvation of the proteins, and is within a range of solutes affecting solubility of the proteins. It is yet to be investigated as to whether transported $NH_4^+$ in the peritubular capillaries from the medullary tissues is to be combined with free $PO_4^{3-}$ present in the blood in a form of $(NH_4)_3PO_4$, whether concentration of $(NH_4)_3PO_4$ in patients with an elevated concentration of $PO_4^{3-}$ in the blood due to chronic renal failure continues to be below 0.15M~0.5M, thereby favoring an unfolded configuration of the tertiary structure of the blood proteins, or whether the concentration of $(NH_4)_3PO_4$ in the patients with the elevated concentration of $PO_4^{3-}$ in the blood due to the chronic renal failure is above the threshold for the solubility of the protein, thereby promoting a folded configuration of the tertiary structure of the blood proteins. It also stands to reason that unfolded blood proteins in a proximal portion of the peritubular capillaries associated with a sudden lowering of pH of the blood due to the glomerular filtration of bicarbonate from the blood need to be refolded in a distal portion of the peritubular capillaries after having released the protein bound uremic toxins back to their nascent tertiary configuration for proper functioning before returning back to systemic circulation. This refolding process of the blood proteins can be accomplished by reabsorbing bicarbonate in the distal portion of the peritubular capillaries, thus normalizing pH of the blood. The refolding process can be assisted by ammonia per se transported into the distal portion of the peritubular capillaries from the medullary tissues, as ammonia ($NH_4^+$) is the most effective cation in the Hofmeister series on maintaining folded configuration of the tertiary structure of proteins. By this logic, there would be an advantage of adding ammonia to a dialysate at a concentration similar to that found in the blood, near a distal end of a hemodialyzer and a hemodiafiltrator just prior to sending hemodialyzed/hemodiafiltrated blood back to the systemic circulation of a patient. The refolded blood proteins in the systemic circulation, with their binding sites being emptied by the hemodialysis or the hemodiafiltration, then should be able to absorb the protein bound uremic toxins from the free fraction in the blood. Obviously patients with liver disorders or inherited disorder of ammonia metabolism cannot receive any additional ammonia during hemodialysis and hemodiafiltration as an increased level of ammonia in the systemic circulation may induce serious harm to the patients.

In a clinical scenario of a patient in a metabolic acidosis and uremia due to a significant renal failure undergoing the hemodialysis or the hemodiafiltration, a following sequence of biochemical changes would occur: 1. Excess level of metabolic acids and an excess concentration of blood urea in vivo, promoting release of the protein bound uremic toxins from the binding proteins to become the freed protein bound uremic toxins in circulation and inside cells in vivo, thus inciting damages to exposed tissues and the cells; 2. Immediate correction of a pH of an acidified blood by the metabolic acidosis by the hemodialysis (including the hemodiafiltration) with a bicarbonate-rich dialysate and a rapid reduction of the concentration of the blood urea by said hemodialysis and hemodiafiltration, making the freed protein bound uremic toxins bound back to the binding sites of the proteins; 3. Return of a dialyzed/diafiltrated blood in a normal pH and a reduced blood urea having the protein bound uremic toxins fully bound to the binding sites of the binding protein to the patient; 4. Mixing of the dialyzed blood in the normal pH and the reduced blood urea with the acidified blood having the excess blood urea occurs in the systemic circulation, thereby lowering the pH of the dialyzed blood in vivo and increasing the concentration of the blood urea from the reduced level, thereby freeing the protein bound uremic toxins from the binding proteins and releasing them back to the patient; 5. Largely unchanging concentrations of the freed protein bound uremic toxins in the circulation and the cells in vivo; 6. Ongoing toxicity from the protein bound uremic toxins despite the hemodialysis and the hemodiafiltration.

Based on the aforementioned biochemical and physiologic understanding on changes in the concentration of the protein bound uremic toxins from a perspective of the folding and unfolding the tertiary structure of the blood proteins, I propose a dual chambered hemodiafiltrator for hemodiafiltration that allows sequential increase from 6.0 to 8.0 in pH of dialysates across iso-electric points of the blood proteins, that allows sequential gradient transition in urea concentration of the dialysate going through the hemodiafiltrator from a level equivalent to a patient's concentration of the blood urea at a time of the hemodiafiltration to no urea, and that allows addition of ammonia in the dialysate to a blood level of ammonia expected in a normal individual (20~25 micro-mol/L) immediately prior to sending the dialyzed blood back to the systemic circulation of the patient. The dual chambered hemodiafiltrator comprises two compartments for the dialysates, in which one packed bundle of hollow fibers for blood flow is coaxially placed. A first compartment is configured to retain and run a first dialysate which comprises an acidic pH dialysate, urea at a transitioning concentration over time from an initial concentration equivalent to or slightly less than a concentration of the blood urea in the patient at start of a session of hemodiafiltration to a zero concentration at conclusion of the session of the hemodiafiltration; a second compartment is configured to retain and run a second dialysate which comprises a basic pH dialysate, and no urea and a concentration of ammonia up to a normal level of ammonia found in normal individuals (20~25 micro-mol/L).

The first and the second compartmentalized dialysate chambers are separated by an inner circumferential rim circumferentially protruding from an inner tubular wall of a tubular housing toward the packed bundle of the hollow fibers. The packed bundle of the hollow fibers are provided in a doughnut configuration on a radial cross-section, comprising an open central tubular column encircled by a plurality of the hollow fibers arranged in a cylindrical configuration. About a mid-to-distal point of the open central tubular column, there is provided a coaxial cone disk occluding the open central tubular column, thereby compartmentalizing the open central tubular column into a first open central tubular column and a second open central tubular column. The inner circumferential rim inside the tubular housing of the hemodiafiltrator divides an outer circumferential cylindrical space encircling an outer peripheral layer of the packed bundle of the hollow fibers into a first (proximal) outer circumferential space and a second (distal) outer circumferential space, so as to compartmentalize the dialysate chamber into the first and the second compartmentalized dialysate tubular chamber. The coaxial cone disk is configured to occlude the mid-to-distal point of the open central tubular column so as to not only compartmentalize the open central tubular column into the first and the second portion of the open central tubular column, but also change a direction of an incoming dialysate flow through the open central tubular column to a reverse direction of an outgoing dialysate flow across the packed bundle of the hollow fibers through the outer circumferential space. The first dialysate is configured to flow in the first open central tubular column of the packed bundle of the hollow fibers through a first central dialysate intake tube, radially goes through the packed bundle of the hollow fibers disposed inside the first dialysate chamber, and comes out into the first outer circumferential space. The first dialysate in the first outer circumferential space then is pulled up through a first dialysate output tube that is open to the first outer circumferential space. The first central dialysate intake tube is coaxially disposed inside the first dialysate output tube along a longitudinal axis in a coaxial tube-in-tube configuration. There is a reversal of a dialysate flow direction at the inner circumferential rim whereby a first dialysate flow axially flowing in the first open central tubular column toward the coaxial cone disk is coaxially pulled out through the first outer circumferential space and drained through the first dialysate output tube but in a 180-degree opposite direction to the flow direction of the first dialysate in the first open central tubular column. The second compartmentalized dialysate chamber is configured in the same way as the first compartmentalized dialysate chamber but disposed on an opposite side to the first compartmentalized dialysate chamber.

SUMMARY OF THE INVENTION

In one embodiment, the present hemodiafiltrator comprises a first dialysate conduit, a second dialysate conduit, and a mid tubular cylinder which is compartmentalized into a mid dialysate tubular cylinder, and a blood compartment having a proximal blood chamber and a distal blood chamber. The first dialysate conduit distally adjoins a proximal portion of the mid tubular cylinder along a longitudinal axis of the hemodiafiltrator, and the second dialysate conduit proximally adjoins a distal portion of the mid tubular cylinder along the longitudinal axis. A packed bundle of hollow fibers for blood flow of the blood compartment is enclosed coaxially inside the mid dialysate tubular cylinder in between the proximal and the distal blood chamber. The mid dialysate tubular cylinder is axially disposed in the middle of the hemodiafiltrator, adjoining proximally the proximal blood chamber and distally the distal blood chamber.

In one embodiment, the mid dialysate tubular cylinder is compartmentalized by an inner circumferential rim protruding from an inner tubular wall of the mid dialysate tubular cylinder into proximal (first) and distal (second) compartmentalized dialysate chambers arranged in tandem along the longitudinal axis. The first compartmentalized dialysate chamber of the mid dialysate tubular cylinder adjoins proximally the first dialysate conduit, and the second compartmentalized dialysate chamber adjoins distally the distal blood conduit. The packed bundle of the hollow fibers is provided in a doughnut configuration on a radial cross section as a cylindrical tubular structure having an open central tubular column along a longitudinal axis of the packed bundle of the hollow fibers. The open central tubular column is compartmentalized into proximal and distal open central tubular columns of the open central tubular column by a coaxial cone disk occluding a portion of the open central tubular column.

In one embodiment, both the first and second dialysate conduits are provided in a coaxial tube-in-tube configuration with a first outer conical reservoir conduit coaxially enclosing a first inner longitudinal tubular conduit and a second outer conical reservoir conduit coaxially enclosing a second inner longitudinal tubular conduit, respectively. Each inner longitudinal tubular conduit is leakproofly inserted coaxially through a central portion of each blood compartment into each portion of the open central tubular column of the packed bundle of the hollow fibers, so as to establish an intake route for a dialysate. Each outer conical reservoir conduit adjoins a portion of the mid tubular cylinder in a way each compartmentalized dialysate chamber is configured to drain the dialysate from each compartmentalized dialysate chamber to each outer conical reservoir conduit. The first dialysate conduit adjoining the first compartmentalized dialysate chamber establishes a first dialysate chamber of the dual chamber of the hemodiafiltrator; the second dialysate conduit adjoining the second compartmentalized dialysate chamber establishes a second dialysate chamber. A first incoming dialysate flow in the first dialysate chamber is configured to move distally, whereas a second incoming dialysate flow in the second dialysate chamber configured to move proximally in an opposite direction to that of the first dialysate flow In one embodiment, the proximal blood chamber leakproofly encircles a proximal portion of the packed bundle of the hollow fibers, and the distal blood chamber leakproofly encircles a distal portion of the packed bundle of the hollow fibers. The proximal blood chamber is coaxially aligned with the distal blood chamber, and both the proximal and distal blood chambers are coaxially aligned with the packed bundle of the hollow fibers. A blood intake tube radially adjoins the proximal blood chamber and a blood output tube radially adjoins the distal blood chamber, so as to establish a path of the blood flow from the blood intake tube through the packed bundle of the hollow fibers to the blood output tube.

In one embodiment, the mid dialysate tubular cylinder coaxially encloses the packed bundle of the hollow fibers. A compartmentalized configuration of the tandem arrangement of the compartmentalized dialysate chambers comprises the first compartmentalized dialysate chamber for hemodiafiltration and acidification of blood going through the proximal portion of the packed bundle of the hollow fibers by a first dialysate having a low concentration of bicarbonate and a urea at a transitioning concentration over time from an initial concentration at start of a session of hemodiafiltration equivalent to or slightly less than a concentration of the blood urea in a patient to a zero concentration at conclusion of the session of the hemodiafiltration; the second compartmentalized dialysate chamber for hemodiafiltration and normalization of a pH of the blood in a distal portion of the packed bundle of the hollow fibers by a second dialysate having a higher concentration of bicarbonate than the first dialysate. The second dialysate contains no urea but ammonia at a concentration of 20~25 micro-mol/L. Each compartmentalized dialysate chamber longitudinally adjoins and is compartmentalized from each other compartmentalized dialysate chamber by the inner circumferential rim protruding from the inner tubular wall of the mid dialysate tubular cylinder.

In one embodiment, a diameter of an inner margin of the inner circumferential rim is shorter than a diameter of the inner tubular wall of the compartmentalized dialysate chambers by at least 1 mm so as to provide an outer circumferential space of a measurable dimension between an outer peripheral layer of the packed bundle of the hollow fibers and an inner tubular wall of the mid dialysate tubular cylinder. The inner circumferential rim is provided in a rectangular bar configuration on a longitudinal cross section. A diameter of the inner circumferential rim is nearly equivalent to a diameter of the packed bundle of the hollow fibers, so as to tightly encircle a portion of the outer peripheral layer of the packed bundle of the hollow fibers. The outer circumferential space serves as compartmentalized reservoir to retain the dialysate which runs through the outer circumferential space of each compartmentalized dialysate chamber from each inner longitudinal tubular conduit to each outer conical reservoir conduit of each dialysate conduit. The inner circumferential rim divides the outer circumferential space of the mid dialysate tubular cylinder into a proximal (first) portion of the outer circumferential space and a distal (second) portion of the outer circumferential space.

In one embodiment, the packed bundle of the hollow fibers contains about 10,000 hollow fibers, with an inner diameter of each wet fiber measuring about 200 micrometer, a membrane thickness measuring about 20-45 micrometer, and a length measuring 80-240 mm. Polymers for the hollow fibers comprise Cuprophan, Cellulose diacetate, Cuproammonium rayon, Hemophan, Polysulfone, Polycarbonate, Cellulose triacetate, Polyamide, Polyethersulfone, Polyacrilonitrile, or Polymethylmethacrylate. The packed bundle of the hollow fibers is coaxially placed inside the mid tubular dialyzer compartment, wherein an outer peripheral layer of a proximal portion of the packed bundle of the hollow fibers housed in the mid tubular dialyzer compartment is leakproofly encased by a distal portion of a tubular cylinder of the proximal blood compartment, and wherein an outer peripheral layer of a distal portion of the packed bundle of the hollow fibers is leakproofly encased by a proximal portion of a tubular cylinder of the distal blood compartment.

In one embodiment, the packed bundle of the hollow fibers is provided in the doughnut configuration on the radial cross-section having an empty column of the open central tubular column circumferentially surrounded by a plurality of the hollow fibers longitudinally stacked up in a cylindrical configuration. A first set of resiliently stiff inner string harness in a tubular configuration is insertably placed inside the open central tubular column so as to provide said open central tubular column with a structural strength. A second set of elastomeric string harness in a tubular configuration is provided around the outer peripheral layer of the packed bundle of the hollow fibers to tie up said packed bundle of the hollow fibers. Along a longitudinal length of the inner string harness close to the distal portion of the packed bundle of the hollow fibers, the coaxial cone disk in a pointed cone configuration is fixedly attached to the inner string harness in a way the coaxial cone disk occludes completely the portion of the open central tubular column, thereby compartmentalizing the open central tubular column into the proximal (first) and distal (second) open central tubular columns of the open central tubular column. An outer conical surface of the coaxial cone disk facing a distal portion of the open central tubular column has a tip pointed toward a distal portion of the open central tubular column and an inner surface of the coaxial cone disk facing a proximal portion of the open central tubular column has a conical depression.

In one embodiment, the packed bundle of the hollow fibers is tightly encircled by the inner circumferential rim about the outer peripheral layer of the packed bundle of the hollow fibers. A proximal (first) portion of the packed bundle of the hollow fibers disposed proximal to the inner circumferential rim is encased in the first compartmentalized dialysate chamber of the mid dialysate tubular cylinder and a distal (second) portion of the packed bundle of the hollow fibers disposed distal to the inner circumferential rim is encased in the second compartmentalized dialysate chamber of the mid dialysate tubular cylinder. The proximal (first) portion of the packed bundle of the hollow fibers continues to become the distal (second) portion of the packed bundle of the hollow fibers across the inner circumferential rim.

In one embodiment, there is provided a measurable longitudinal distance between a base portion of the coaxial cone disk of the inner string harness disposed inside the open central tubular column and the inner circumferential rim protruding from the inner tubular wall of the mid dialysate tubular cylinder. The longitudinal distance between the base portion of the coaxial cone disk and the inner circumferential rim is configured to provide a transitional region of the packed bundle of the hollow fibers in a proximal portion of the distal (second) portion of the packed bundle of the hollow fibers. The transitional region of the packed bundle of the hollow fibers is three dimensional and coaxially aligned with a longitudinal axis of the packed bundle of the hollow fibers. The transitional region of the packed bundle of the hollow fibers is configured as a transverse cross-sectional columnar region of the packed bundle of the hollow fibers established between the base portion of the coaxial cone disk and the inner circumferential rim, and serves as a region whereby the first dialysate gets mixed with the second dialysate.

In one embodiment, the first dialysate flows through the first inner longitudinal tubular conduit of the first dialysate conduit to the proximal (first) open central tubular column of the open central tubular column of the packed bundle of the hollow fibers. The second dialysate proximally flows through the second inner longitudinal tubular conduit of the second dialysate conduit to the distal (second) open central tubular column of the open central tubular column of the packed bundle of the hollow fibers. Flow direction of the first dialysate in the proximal (first) open central tubular column is distal toward the inner surface of the coaxial cone disk, and flow direction of the second dialysate in the distal (second) open central tubular column is proximal toward the outer conical surface of the coaxial cone disk. The coaxial cone disk is disposed in a proximal part of the distal (second) open central tubular column, whereas the inner circumferential rim is disposed close to the proximal portion of the first compartmentalized dialysate chamber. At the inner surface of the conical depression of the coaxial cone disk disposed thereof in the distal (second) open central tubular column separated by the longitudinal distance from the inner circumferential rim, the first dialysate is deflected off in a plurality of acute angles: a portion of the first dialysate deflected off then goes through individual hollow fibers of the proximal (first) portion of the packed bundle of the hollow fibers at the acute angles into the proximal (first) portion of the outer circumferential space and another portion of the first dialysate deflected off goes through the proximal portion of the distal (second) portion of the packed bundle of the hollow fibers into the distal (second) portion of the outer circumferential space. The second dialysate inside the distal (second) open central tubular column is deflected off on the outer conical surface of the coaxial cone disk in a plurality of obtuse angles, thereby the entire second dialysate goes through individual hollow fibers of the distal (second) portion of the packed bundle of the hollow fibers into the distal (second) portion of the outer circumferential space. Consequently, the first dialysate in a proximal portion of the distal (second) portion of the outer circumferential space is admixed with the second dialysate. The proximal part of the distal (second) portion of the packed bundle of the hollow fibers disposed between the coaxial cone disk and the inner circumferential rim receives both the first dialysate and the second dialysate which then mixes with the first dialysate. Thus, the transitional region between the base portion of the coaxial cone disk and the inner circumferential rim provides a transitional space between the first and second dialysates. The mixing of the first and second dialysates at the transitional region serves to produce a continuous gradient of the pH and the urea concentration in a dialysate mixture produced by the mixing of the first and second dialysates.

In one embodiment, the protein bound uremic toxins are removed from the blood in the packed bundle of the hollow fibers in the first compartmentalized dialysate chamber and in the transitional region disposed in a proximal part of the second compartmentalized dialysate chamber by the dialysates having low concentrations of bicarbonate in a dialysate proportioning concentration ratio. A pH of the dialysate in the first dialysate chamber would range from approximately 5.0 and 7.0, so as to acidify the blood in the packed bundle of the hollow fibers. A pH of the second dialysate in the second compartmentalized dialysate chamber would range from 7.0 to 9.0 with a high concentration of bicarbonate in the dialysate proportioning concentration ratio, so as to normalize a pH of the blood back to a pH of 7.35-7.45 in the distal (second) portion of the packed bundle of the hollow fibers existing to the blood output tube. A blood pH in the transitional region of the packed bundle of the hollow fibers therefore is configured for a continuous pH gradient from 5.0 to 7.45. In this configuration, the protein bound uremic toxins having iso-electric points ranging from 5.0 to 9.0 of pH would be removed by iso-electric gradient with a successive and continuous stepping up in the pH of the blood along a longitudinal length of the packed bundle of the hollow fibers of the hemodiafiltrator.

In one embodiment, the first dialysate comprises the urea that is separately added to the first dialysate so as to vary the concentration of the urea in the first dialysate over time during the session of the hemodiafiltration. The initial concentration at the start of the session of the hemodiafiltration would range from 20 mg/dL to 100 mg/dL, equivalent to or slightly less than a concentration of the blood urea in the patient, which then decreases over time along with the hemodiafiltration to a zero concentration at the conclusion of the session of the hemodiafiltration. The second dialysate does not have the urea. Therefore, the transitional region of the packed bundle of the hollow fibers establishes a downward gradient in the urea concentration from the first dialysate to the second dialysate.

In one embodiment, a concentration of the ammonia of the second dialysate is up to about 20 micro-mol/L~25 micro-mol/L. Since the first dialysate does not contain the ammonia, an ammonia concentration gradient in the transitional region of the packed bundle of the hollow fibers ranges from zero micro-mol/L to 25 micro-mol/L. The transitional region of the packed bundle of the hollow fibers serves to introduces the ammonia from the first dialysate to the blood in the packed bundle of the hollow fibers in a linear upward gradient configuration.

DETAILED DESCRIPTION OF THE DRAWINGS

As described below, the present invention provides a centrifugal gradient dialysate dual chamber hemodiafiltrator comprising a first dialysate conduit, a second dialysate conduit, and a mid tubular cylinder which is compartmentalized into a proximal blood chamber, a mid dialysate tubular cylinder, and a distal blood chamber. The mid dialysate tubular cylinder is compartmentalized by an inner circumferential rim protruding from an inner tubular wall of the mid dialysate tubular cylinder into two compartmentalized dialysate chambers arranged in tandem along the longitudinal axis of the hemodiafiltrator. A packed bundle of hollow fibers for blood flow is enclosed coaxially along a longitudinal axis inside the mid dialysate tubular cylinder. The packed bundle of the hollow fibers is provided in a doughnut configuration on a radial cross section as a cylindrical tubular structure having an open central tubular column along a longitudinal axis of the packed bundle of the hollow fibers. The open central tubular column is compartmentalized into proximal and distal portions of the open central tubular column by a coaxial cone disk occluding a portion of the open central tubular column. It is to be understood that the descriptions are solely for the purposes of illustrating the present invention, and should not be understood in any way as restrictive or limited. Embodiments of the present invention are preferably depicted with reference to FIGS. 1 to 9, however, such reference is not intended to limit the present invention in any manner. The drawings do not represent actual dimension of devices, but illustrate the principles of the present invention.

Figure 1:
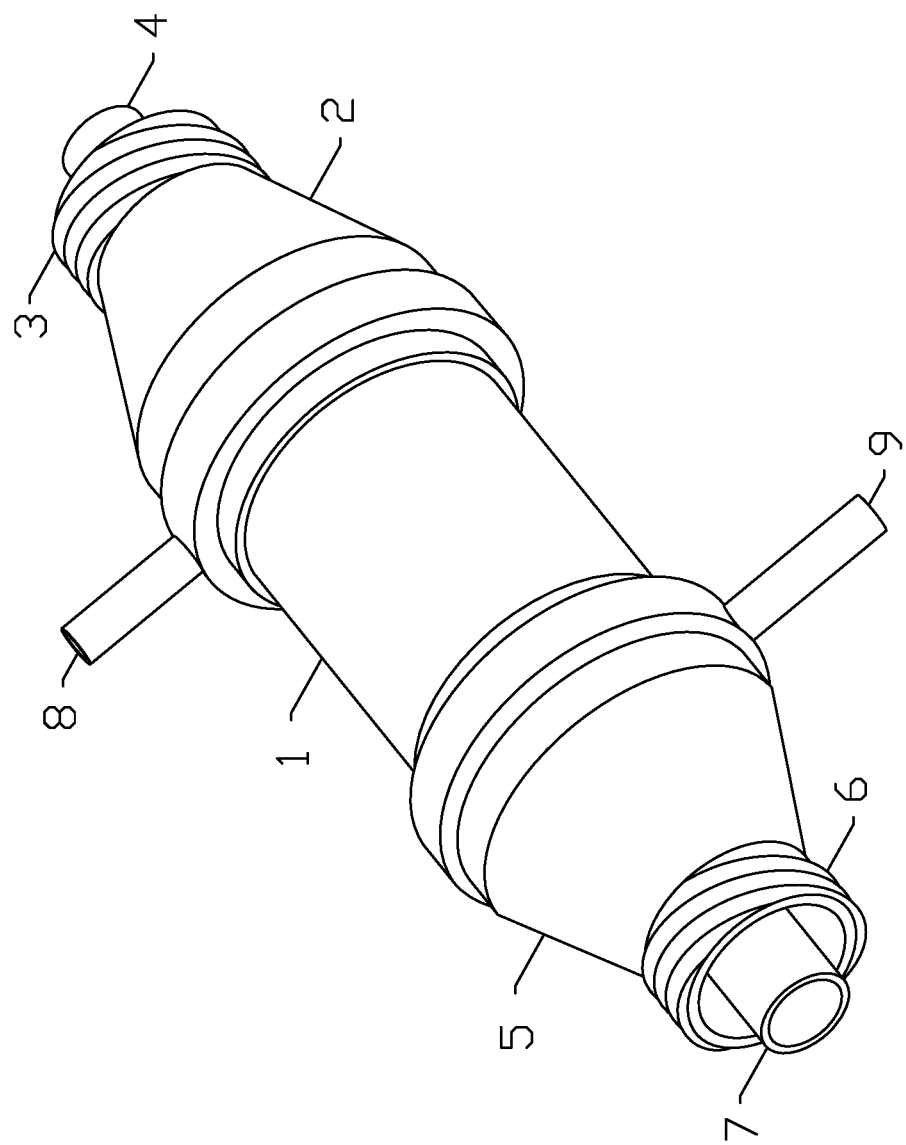
FIG. 1 shows a schematic three-dimensional view of a centrifugal gradient dialysate dual-chamber hemodiafiltrator.

A centrifugal gradient dialysate dual chamber hemodiafiltrator shown in FIG. 1, comprises the mid tubular cylinder 1 provided in a cylindrical configuration, the first (proximal) dialysate conduit 2 in a conically tubular configuration and the second (distal) dialysate conduit 5 in the conically tubular configuration. The first dialysate conduit 2 comprises a proximal external helical tubular cylinder 3 which is a proximal part of a conical reservoir conduit and a proximal portion 4 of a first inner longitudinal tubular conduit coaxially enclosed in the conical reservoir conduit. The second dialysate conduit 5 comprises a distal external helical tubular cylinder 6 which is a proximal part of a conical reservoir conduit and a proximal portion 7 of a second inner longitudinal tubular conduit coaxially enclosed in the conical reservoir conduit. A blood intake tube 8 opens to a proximal blood chamber hidden inside a proximal portion of the mid tubular cylinder 1, and a blood output tube 9 opens to a distal blood chamber hidden inside a distal portion of the mid tubular cylinder 1.

Figure 2:
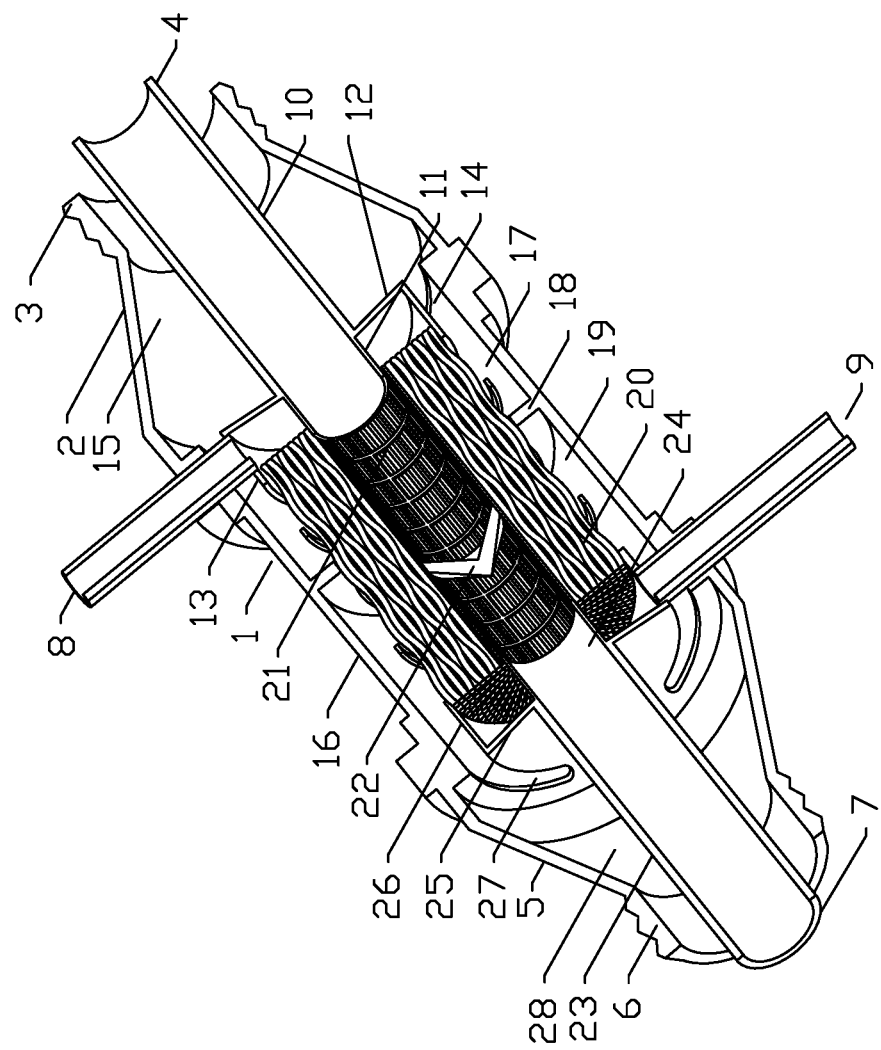
FIG. 2 represents a schematic three-dimensional exposed cut-out view of the centrifugal gradient dialysate dual-chamber hemodiafiltrator in an assembled configuration.

FIG. 2 represents a schematic three-dimensional exposed cut-out view of the centrifugal gradient dialysate dual chamber hemodiafiltrator in an assembled configuration. The mid tubular cylinder 1 of the centrifugal gradient dialysate dual chamber hemodiafiltrator comprises a proximal blood chamber 12 and a distal blood chamber 25. The proximal blood chamber 12, provided in a doughnut configuration on a radial cross section, is concentrically divided into a proximal outer tubular columnar space 13 and an inner tubular columnar space by a proximal inner coaxial tubular cylinder 11 of the proximal blood chamber 12. The distal blood chamber 25, similarly provided as in the doughnut configuration on the radial cross section, is concentrically divided into a distal outer tubular columnar space 26 and a distal inner tubular columnar space 24. The proximal outer tubular columnar space 13 fixedly encircles a proximal part of the packed bundle of the hollow fibers 20, and the distal outer tubular columnar space 26 fixedly encircles a distal part of the packed bundle of the hollow fibers 20. The blood intake tube 8 radially opens to the proximal blood chamber 12, and the blood output tube 9 radially opens to the distal blood chamber 25 in an opposite side to the blood intake tube 8, so as to establish a diagonal blood flow through the packed bundle of the hollow fibers 20. The proximal inner coaxial tubular cylinder 11 of the proximal blood chamber 12 proximally adjoins the first inner longitudinal tubular conduit 10, and is distally inserted in a proximal part of an open central tubular column 21 of a packed bundle of hollow fibers 20 in a leakproof way. The distal inner coaxial tubular cylinder 24 of the distal blood chamber 25 distally adjoins the second inner longitudinal tubular conduit 23, and is proximally inserted in a distal part of an open central tubular column 21 of the packed bundle of the hollow fibers 20 in the leakproof way. The inner coaxial tubular cylinders 11 and 24 are provided a a conduit for dialysate.

The first dialysate conduit 2 shown in FIG. 2 comprises a first conical reservoir conduit 15 proximally opening to the proximal external helical tubular cylinder 3 and the first inner longitudinal tubular conduit 4 coaxially placed in the first conical reservoir conduit 15. At an adjoined part between the first dialysate conduit 2 and a proximal portion of a mid dialysate tubular cylinder 16, there is provided an upper radial wall of the mid dialysate tubular cylinder compartmentalizing the first dialysate conduit 2 from the proximal portion of the mid dialysate tubular cylinder 16. The upper radial wall serves as a roof of the proximal blood chamber 12. The upper radial wall comprises a plurality of proximal curvilinear fenestrations disposed thereof around an outer perimeter of said upper radial wall. The first conical reservoir conduit 15 communicates with a first outer circumferential space 17 of the mid dialysate tubular cylinder 16 of the mid tubular cylinder 1 through the plurality of the proximal curvilinear fenestrations 14. An inner circumferential rim 18 of the mid dialysate tubular cylinder 16 divides an outer circumferential space of the mid dialysate tubular cylinder 16 into the first outer circumferential space 17 and a second outer circumferential space 19. The second dialysate conduit 5 comprises a second conical reservoir conduit 28 distally opening to the distal external helical tubular cylinder 6 and the second inner longitudinal tubular conduit 7 coaxially placed in the second conical reservoir conduit 28. At an adjoined part between a proximal portion of the second dialysate conduit 5 and a distal portion of the mid dialysate tubular cylinder 16, there is provided a lower radial wall of the mid dialysate tubular cylinder 16 compartmentalizing the proximal portion of the second dialysate conduit 5 from the distal portion of the mid dialysate tubular cylinder 16. The lower radial wall serves as a roof of the distal blood chamber 25. The lower radial wall comprises a plurality of distal curvilinear fenestrations disposed thereof around an outer perimeter of said distal radial wall. The second conical reservoir conduit 28 communicates with the second outer circumferential space 19 of a mid dialysate tubular cylinder 16 of the mid tubular cylinder 1 through the plurality of the distal curvilinear fenestrations 27. The first inner longitudinal tubular conduit 10 protrudes as the proximal portion 4 from the proximal external helical tubular cylinder 3, and distally adjoins the proximal inner coaxial tubular cylinder 11 of the proximal blood chamber 12. The second inner longitudinal tubular conduit 23 protrudes as the distal portion 7 from the distal external helical tubular cylinder 6, and proximally adjoins the distal inner tubular columnar space 24 of the distal blood chamber 25. A coaxial cone disk 22 is occlusively placed in a mid-to-distal point of the open central tubular column 21, so as to compartmentalize the open central tubular conduit 21 into proximal and distal open central tubular conduits and to change a direction of an incoming dialysate flow through the open central tubular column 21 to a reverse direction of an outgoing dialysate flow across the packed bundle of the hollow fibers 20 through the outer circumferential spaces 17 and 19.

Shown in FIG. 2, the first and second outer circumferential spaces 17 and 19 are provided between an outer peripheral layer of the packed bundle of the hollow fibers 20 and an inner tubular wall of the mid dialysate tubular cylinder 16, compartmentalized by the inner circumferential rim 18. The first and second outer circumferential spaces 17 and 19 are configured to serve as reservoir of the dialysate. A dimension of each outer circumferential space is determined by a radial length (height) of the inner circumferential rim 18. The radial length is not less than 0.5 mm so as to provide each outer circumferential space a measurable dimension between the outer peripheral layer of the packed bundle of the hollow fibers 20 and the inner tubular wall of each compartmentalized dialysate chamber. An innermost part of the inner circumferential rim 18 is configured to come into tight contact with the outer peripheral layer of the packed bundle of the hollow fibers 20, in order to separate each outer circumferential space of the compartmentalized dialysate chamber from each other. In this configuration, a dialysate in each outer circumferential space does not get mixed with the other dialysate in the other circumferential space across the inner circumferential rim 18, except that the dialysates can diffuse through interfibrillar spaces in between individual hollow fibers of the packed bundle of the hollow fibers 20.

Figure 3:
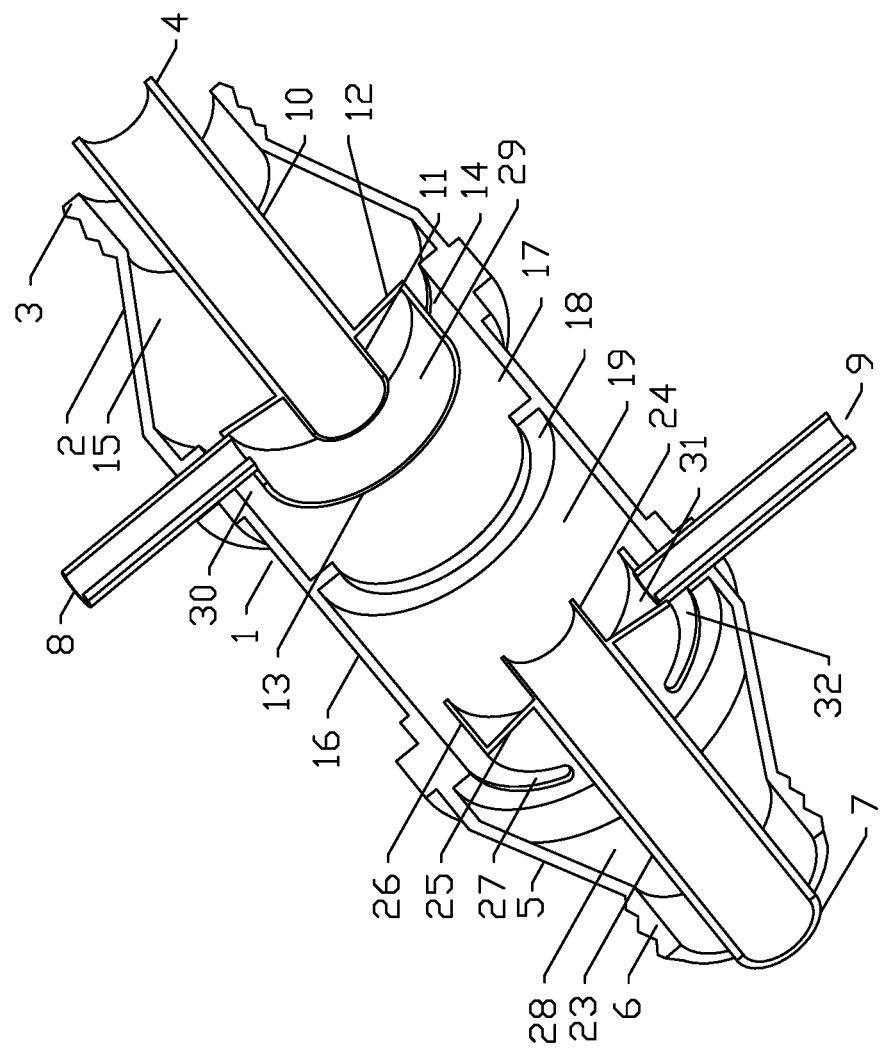
FIG. 3 illustrates a schematic three-dimensional exposed cut-out view of an outer shell.

FIG. 3 illustrates a schematic three-dimensional exposed cut-out view of an outer casing of the centrifugal gradient dialysate dual chamber hemodiafiltrator without the packed bundle of the hollow fibers. The blood intake tube 8 adjoins and opens to a cylindrical tubular space 29 of the proximal outer tubular columnar space 13, of the proximal blood chamber 12. The blood output tube 4 adjoins and opens to a cylindrical tubular space 31, bordered by the distal outer tubular columnar space 26 of the distal blood chamber 25. The mid dialysate tubular cylinder 16 of the mid tubular cylinder 1 is divided by the inner circumferential rim 18 into two compartmentalized dialysate chambers. The first dialysate conduit 2 comprises the first conical reservoir conduit 15 proximally opening to the proximal external helical tubular cylinder 3 and the proximal portion 4 of the first inner longitudinal tubular conduit 10 coaxially placed in the first conical reservoir conduit 15 in a coaxial tube-in-tube configuration. The first conical reservoir conduit 15 communicates with the first outer circumferential space 17 through the plurality of the proximal curvilinear fenestrations 14 and 30. The first inner longitudinal tubular conduit 10 protrudes as the proximal portion 4 from the proximal external helical tubular cylinder 3, and distally adjoins the proximal inner coaxial tubular cylinder 11 of the proximal blood chamber 12. The second dialysate conduit 5 comprises the second conical reservoir conduit 28 distally opening to the distal external helical tubular cylinder 6 and the second inner longitudinal tubular conduit 7 coaxially placed in the second conical reservoir conduit 28 in the coaxial tube-in-tube configuration. The second conical reservoir conduit 28 communicates with the second outer circumferential space 19 through the plurality of the distal curvilinear fenestrations 27 and 32. The second inner longitudinal tubular conduit 23 protrudes as the distal portion 7 from the distal external helical tubular cylinder 6, and proximally adjoins the distal tubular column 24 of the distal blood chamber 25.

FIGS. 4A-4D show the packed bundle of hollow fibers 20 comprising the individual hollow fibers 33 concentrically stacked up from around a first set of resiliently stiff inner string harness 34 abuttingly disposed on a perimeter 36 of the open central tubular column 21 shown in FIG. 2, thus forming the packed bundle of hollow fibers 20 as a cylindrical tube in a doughnut configuration. The first set of the resiliently stiff inner string harness 34 comprises a plurality of circular strings 37 and a plurality of longitudinal strings 38. The plurality of the longitudinal strings 38 fixedly adjoin the plurality of the circular strings 37, so as to impart a structural strength. The first set of the resiliently stiff inner string harness 34 in a tubular configuration provides said open central tubular column 21 with a structural strength so as to avoid inward collapse of the open central tubular column 21. The first set of resiliently stiff inner string harness 34 comprises the coaxial cone disk 22 which is fixedly and coaxially attached to a portion of the plurality of longitudinal strings 38 and to a single string of the circular string 37. The coaxial cone disk 22 occludes completely the portion of the first set of the resiliently stiff inner string harness 34, so as to compartmentalize the open central tubular column 21 into proximal and distal compartmentalized open central tubular columns. A second set of elastomeric outer string harness 35 in a tubular configuration is provided on an outer peripheral layer of the packed bundle of the hollow fibers 20 to securely tie up said packed bundle of the hollow fibers. The second set of the elastomeric outer string harness 35 comprises a mid circular string 39, a proximal circular string 41 and a distal circular string 40, which are fixedly attached to a plurality of a longitudinal strings 42. The mid circular string 39 is configured to tightly encircle the outer peripheral layer of the packed bundle of the hollow fibers 20, whereas the proximal circular string 41 and the distal circular string 40 are configured to be slightly larger in diameter than a diameter of the mid circular string 39. The larger diameter of the proximal circular string 41 and the distal circular string 40 is configured to provide the packed bundle of the hollow fibers 20 with a room to radially distend upon a centrifugal flow of a dialysate from the open central tubular column 21 to the outer peripheral layer of the packed bundle of the hollow fibers 20.

Figure 4A:
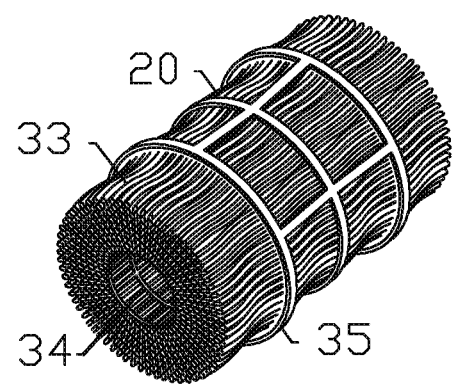
FIGS. 4A-4D depict a schematic illustration of a packed bundle of hollow fibers, an inner string harness, and an outer string harness.
Figure 4B:
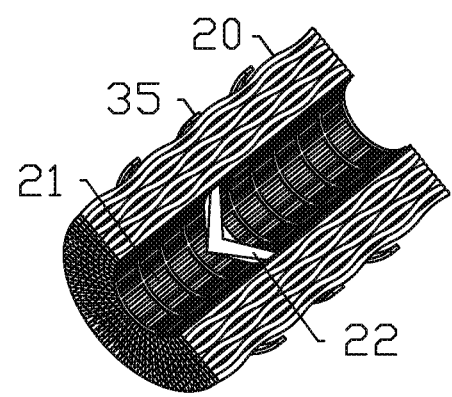
Figure 4C:
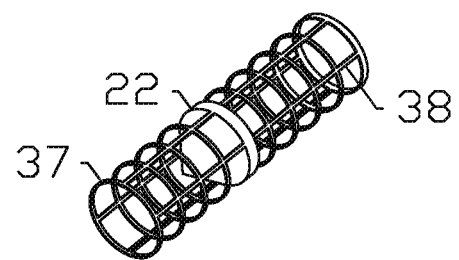
Figure 4D:
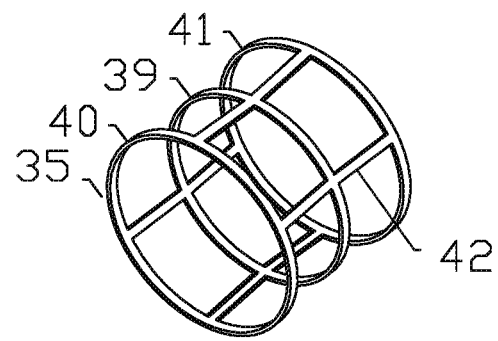
Figure 5A:
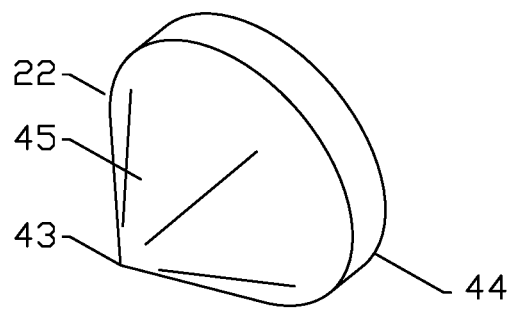
FIGS. 5A-5C show a schematic illustration of a coaxial cone disk of the inner string harness.
Figure 5B:
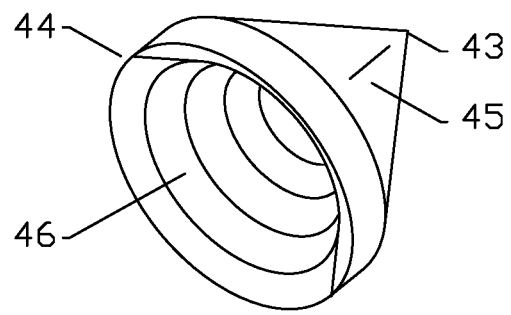
Figure 5C:
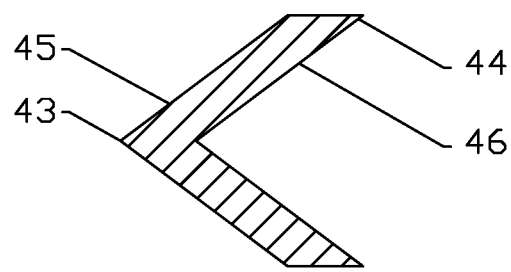

FIG. 5A show a schematic illustration of the coaxial cone disk 22 in a pointed cone configuration comprising a tip 43 and an outer conical surface 45 pointing toward the distal portion of the open central tubular column shown in FIG. 4B, and a base 44 facing the proximal portion of the open central tubular column shown in FIG. 4B. Shown in FIG. 5B, an inner surface 46 of the coaxial cone disk 22 facing the proximal portion of the open central tubular column provides the coaxial cone disk 22 with a conical depression. FIG. 5C shows a two-dimensional profile view of the coaxial cone disk 22 having the tip 43 of the outer conical surface 45, the base 44 and the inner surface 46 in the configuration of the conical depression.

Figure 6A:
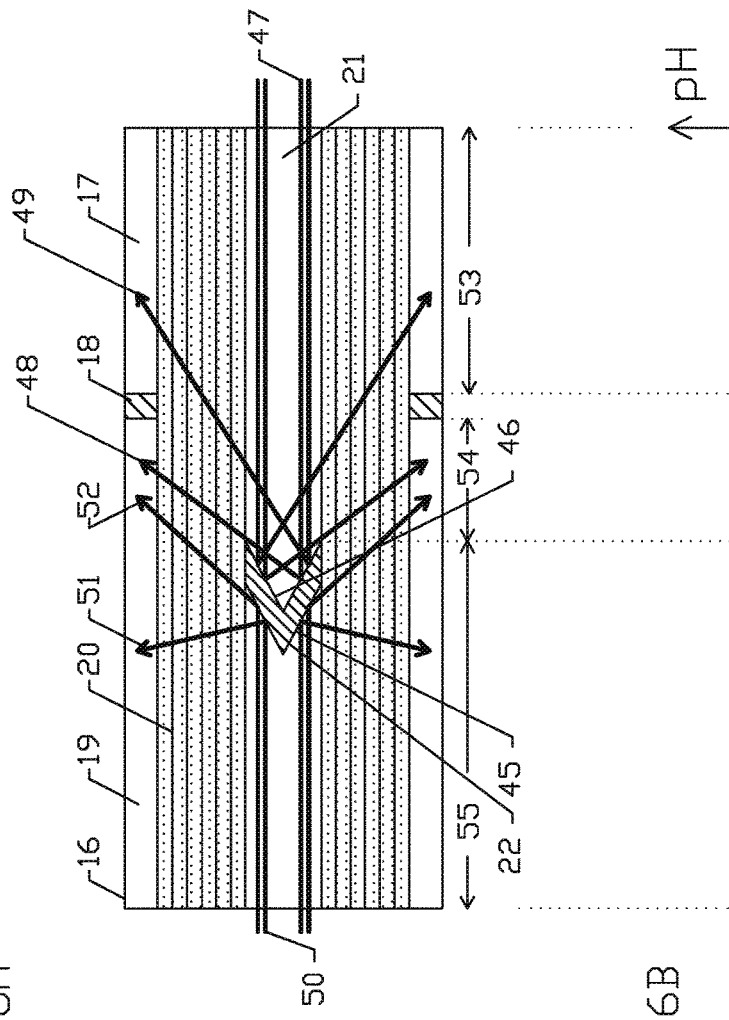
FIGS. 6A-6B shows a schematic illustration of a successive and continuous gradient of pH of the dialysates across the packed bundle of the hollow fibers of the centrifugal gradient dialysate dual-chamber hemodiafiltrator.
Figure 6B:
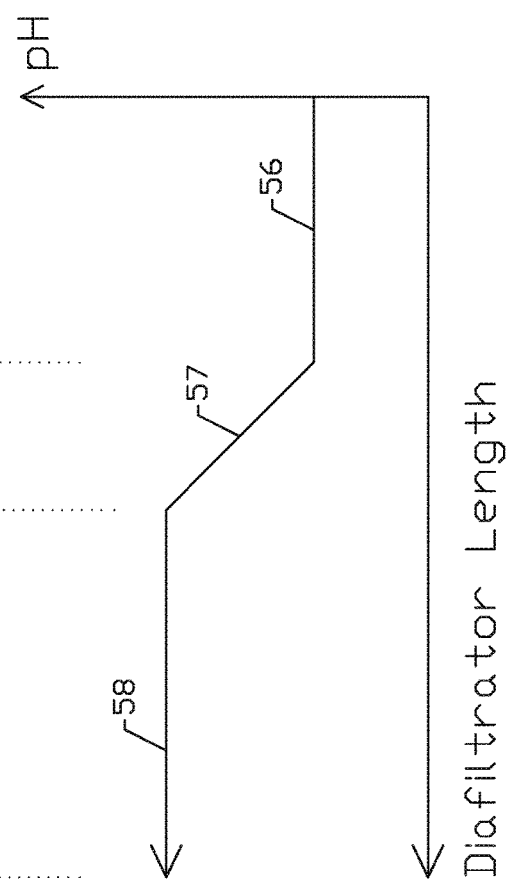

FIG. 6A depicts a schematic presentation of a dialysate flow across the mid dialysate tubular cylinder 16. The coaxial cone disk 22 is disposed in a proximal part of the distal (second) open central tubular column, whereas the inner circumferential rim 18 is disposed away from the coaxial cone disk on a longitudinal axis of the mid dialysate tubular cylinder 16, close to the proximal portion of the packed bundle of the hollow fibers 20. An incoming acidic dialysate 47 into the proximal portion of the open central tubular column 21 heading distally is deflected off the inner surface 46 of the coaxial cone disk 22 at a plurality of acute angles, centrifugally sending a first group of dialysate flow 49 through the packed bundle of the hollow fibers 20 into the first outer circumferential space 17 and a second group of dialysate flow 48 through the packed bundle of the hollow fibers 20 into a proximal portion of the second outer circumferential space 19 disposed distal to the inner circumferential rim 18. An incoming basic (pH) dialysate 50 into the distal portion of the open central tubular column 21 heading proximally is deflected off the outer conical surface 45 of the coaxial cone disk 22 at a plurality of obtuse angles, centrifugally sending a third group of dialysate flow 51 through the packed bundle of the hollow fibers 20 into a distal portion of the second outer circumferential space 19 and a fourth group of dialysate flow 52 through the packed bundle of the hollow fibers 20 into the proximal portion of the second outer circumferential space 19 disposed distal to the inner circumferential rim 18.

Shown in FIG. 6A, the first compartmentalized dialysate chamber 53 receives only the incoming acidic dialysate 47, whereas the second compartmentalized dialysate chamber has two regions: the proximal portion 54 and the distal portion 55. The proximal portion 54 of the second compartmentalized dialysate chamber is defined between the base 44 shown in FIG. 5A of the coaxial cone disk 22 and a distal border of the inner circumferential rim 18. The proximal portion 54 receives a mixture of the incoming acidic dialysate 48 and the incoming basic (pH) dialysate 52, and the distal portion 55 only receives the incoming basic dialysate 51. A pH of the mixture of the dialysate in the proximal portion 54 is in between a pH of the incoming acidic dialysate 48 and a pH of the incoming basic (pH) dialysate 52. Thus, a portion of the packed bundle of the hollow fibers disposed between the base 44 shown in FIG. 5A of the coaxial cone disk 22 and the distal border of the inner circumferential rim 18 enclosed in this three-dimensional volume of the proximal portion 54 of the second compartmentalized dialysate chamber is defined as a transitional region of the current invention. Shown in FIG. 6B, a pH of the incoming acidic dialysate 47 is indicated as 56, and a pH of the incoming basic (pH) dialysate 50 is indicated as 58. Between these two different dialysates, the transitional region serves to produce a mixture of the dialysates having a continuous gradient in pH 57. Similarly, a continuous gradient in ammonia between dialysates is expected in the transitional region (not shown).

Figure 7:
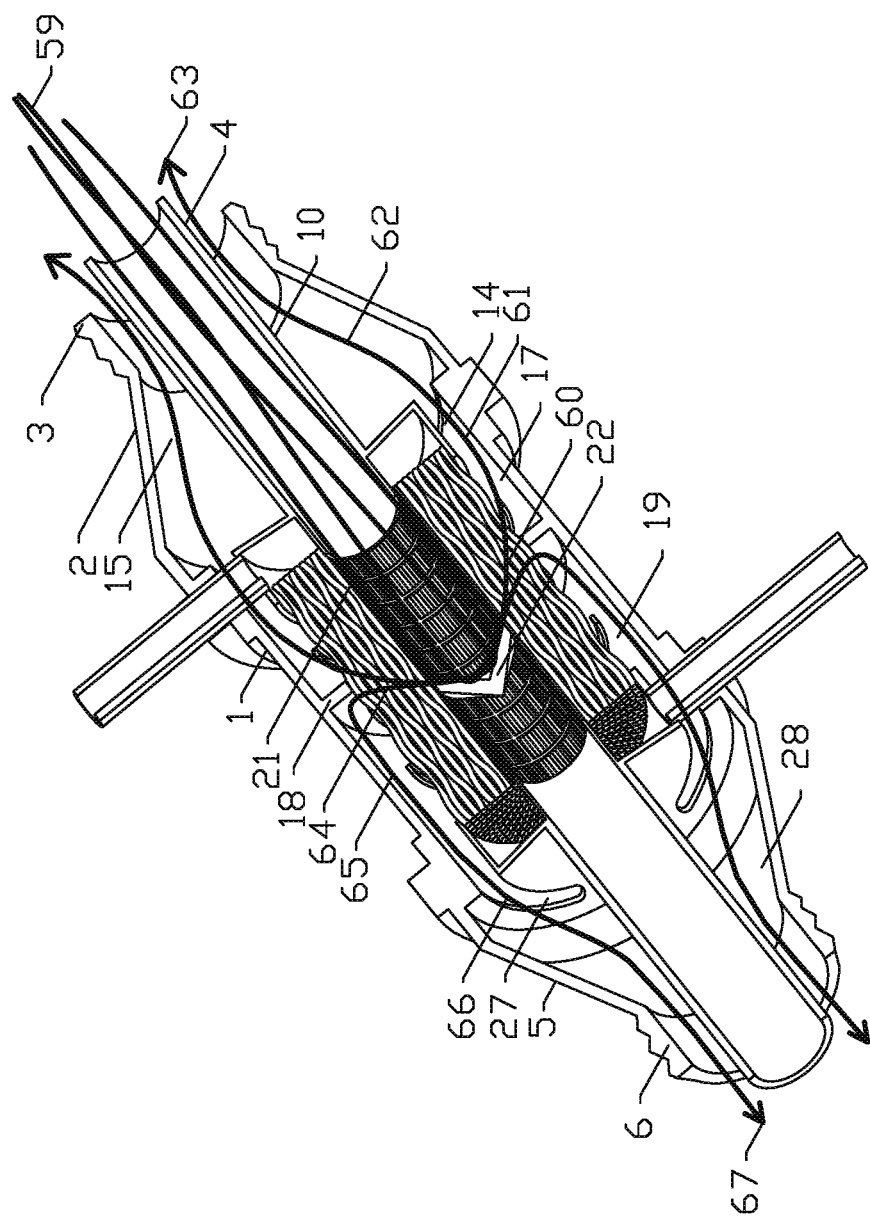
FIG. 7 depicts a schematic example of a flow pattern of a first dialysate in the centrifugal gradient dialysate dual-chamber hemodiafiltrator.

FIG. 7 shows a schematic illustration of a first dialysate flow 59 through the first dialysate conduit distally coming through the proximal portion 4 of the first inner longitudinal tubular conduit 10 of the first dialysate conduit 2 into the proximal portion of the open central tubular column 21. A first part of the dialysate flow 59 is deflected off the conical depression shown in FIG. 5C of the coaxial cone disk 22, changes direction and proximally goes through the proximal portion of the packed bundle of the hollow fibers 20, and then into the first outer circumferential space 17 as a dialysate flow of 60. In fluid dynamics, the dialysate flow 59 having a first dynamic pressure comes to a halt in the distal direction of the dialysate flow 59 and convert to a rotational flow before the dialysate flow 60 having a second dynamic pressure starts to flow in an opposite direction to the distal direction of the dialysate flow 59. An energy of the first dynamic pressure is dissipated as a centrifugal flow of the dialysate across a portion of the packed bundle of the hollow fibers having a defined amount of resistance to the dialysate flow at a time the dialysate flow 59 halts flowing and converts into the rotational flow. To make the dialysate flow 60 move at a same volume per speed but in the opposite direction as that of the dialysate flow 59, an external force needs to be applied to the dialysate flow 60 for the dialysate flow 60 to be pulled in the opposite direction at the same volume per speed. This configuration of a reversal of a flow direction of dialysate across a packed bundle of hollow fibers is to maximize efficiency of centrifugal hemodiafiltration of the dialysate. The dialysate flow 60 then goes through the curvilinear fenestrations 14 as a dialysate flow 61, into the first conical reservoir conduit 15 as a dialysate flow 62, and then out through the proximal external helical tubular cylinder 3 as a dialysate flow 63. The first conical reservoir conduit 15 is provided in a cone configuration, and has a larger volume of space than a volume of space per unit of a longitudinal length in the first compartmentalized dialysate chamber 53 illustrated in FIG. 6A. This configuration is to maintain a higher momentum of the dialysate flow 62 in the first conical reservoir conduit 15 than a momentum of the dialysate flows 60 and 61, so as to reduce variations of the dynamic pressure of the dialysate flows 60 and 61. A second part of the dialysate flow 59 is deflected off the conical depression shown in FIG. 5C of the coaxial cone disk 22, becomes a dialysate flow 64 distally flowing through the packed bundle of the hollow fibers 20, is deflected off a second time at the inner circumferential rim 18, and then becomes a dialysate flow 65 into the proximal portion of the second outer circumferential space 19. The dialysate flow 65 in the second outer circumferential space 19 goes through the curvilinear fenestrations 27 as a dialysate flow 66 into the second conical reservoir conduit 28 of the second dialysate conduit 5. Afterwards, it distally drains out of the distal external helical tubular cylinder 6 as a dialysate flow 67.

Figure 8:
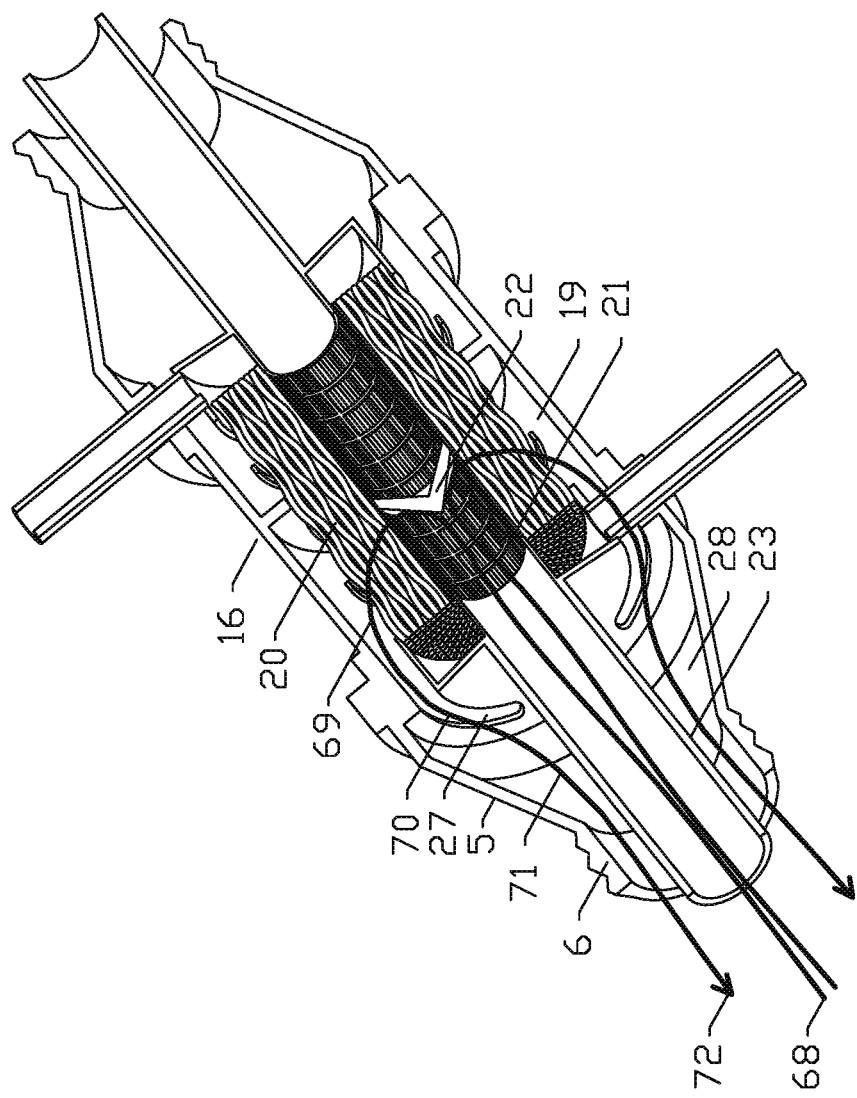
FIG. 8 depicts a schematic example of a flow pattern of a second dialysate in the centrifugal gradient dialysate dual-chamber hemodiafiltrator.

FIG. 8 shows a schematic illustration of a second dialysate flow 68 through the second dialysate conduit proximally coming through the second inner longitudinal tubular conduit 23 of the second dialysate conduit 5 into the distal portion of the open central tubular column 21 toward the coaxial cone disk 22. The second dialysate flow 68 is deflected off at the outer conical surface 45 shown in FIG. 5A of the coaxial cone disk 22, changes direction and distally goes through the distal portion of the packed bundle of the hollow fibers 20, and then into the second outer circumferential space 19 as a dialysate flow of 69. Similar to the dialysate flow 59 converting to the dialysate flow 60 in the first dialysate conduit, the dialysate flow 68 having a first dynamic pressure comes to a halt in the proximal direction of the dialysate flow 68 and convert to a rotational flow before the dialysate flow 69 having a second dynamic pressure starts to flow in an opposite direction to the proximal direction of the dialysate flow 68. An energy of the first dynamic pressure is dissipated as a centrifugal flow of the dialysate across a portion of the packed bundle of the hollow fibers having a defined amount of resistance to the dialysate flow at a time the dialysate flow 68 halts flowing and converts into the rotational flow. To make the dialysate flow 69 move at a same volume per speed but in the opposite direction as that of the dialysate flow 68, an external force needs to be applied to the dialysate flow 69 for the dialysate flow 69 to be pulled in the opposite direction at the same volume per speed. The dialysate flow 69 in the second outer circumferential space 19 goes through the curvilinear fenestrations 27 as a dialysate flow 70, drains into the second conical reservoir conduit 28 of the second dialysate conduit 5 as a dialysate flow 71, and then goes out of the second conical reservoir conduit 28 through the distal external helical tubular cylinder 6 as a dialysate flow 72. Similar to the first conical reservoir conduit 15, the second conical reservoir conduit 28 is provided in a conically tubular configuration, and has a larger volume of space than a volume of space per unit of a longitudinal length in the second compartmentalized dialysate chamber 54+55 illustrated in FIG. 6A. This configuration is to maintain a higher momentum of the dialysate flow 71 in the second conical reservoir conduit 28 than a momentum of the dialysate flows 69 and 70, so as to reduce variations of the dynamic pressure of the dialysate flows 69 and 70.

Figure 9:
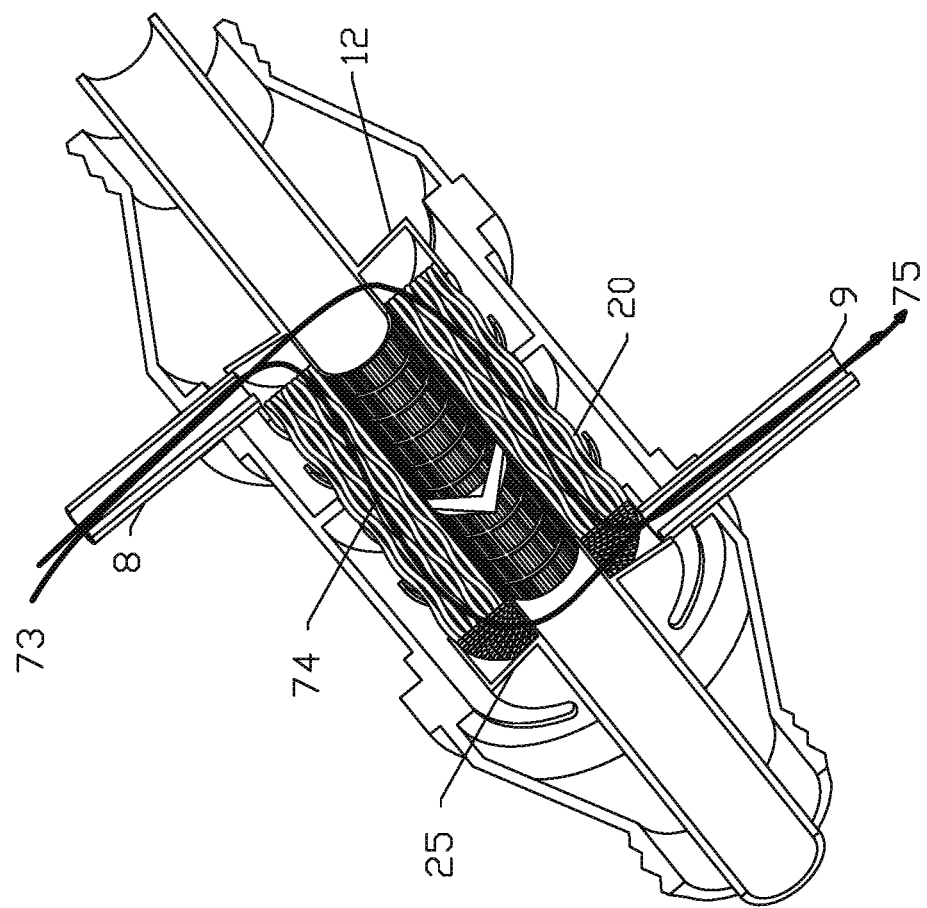
FIG. 9 depicts a schematic example of a flow pattern of blood in the centrifugal gradient dialysate dual-chamber hemodiafiltrator.

FIG. 9 shows a schematic illustration of a blood flow 73 going through the blood intake tube 8 into the proximal blood chamber 12. The blood flow 73 becomes a blood flow 74 which coaxially goes through the packed bundle of the hollow fibers 20 into the distal blood chamber 25, then goes through the blood output tube 9 as a blood flow 75. The blood flow 74 in the proximal portion of the packed bundle of the hollow fibers is countercurrent to the dialysate flow 60 shown in FIG. 7, but concurrent with the dialysate flow 69 shown in FIG. 8.

It is to be understood that the aforementioned description of the centrifugal gradient dialysate dual chamber hemodiafiltrator is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. A centrifugal gradient dialysate dual-chamber hemodiafiltrator for hemodiafiltration, comprising:
   a blood compartment enclosed in a compartmentalized tubular cylinder, comprising a packed bundle of hollow fibers having an open central tubular column in a doughnut configuration on a radial cross-section;
   wherein the open central tubular column is compartmentalized into a proximal portion and a distal portion by a coaxial cone disk radially occluding a portion of the open central tubular column;
   the compartmentalized tubular cylinder, comprising a first dialysate conduit, a mid dialysate tubular cylinder and a second dialysate conduit;
   wherein an inner circumferential rim protruding from an inner tubular wall of the mid dialysate tubular cylinder divides the mid dialysate tubular cylinder into a proximal portion of the mid dialysate tubular cylinder and a distal portion of the mid dialysate tubular cylinder;
   wherein the first dialysate conduit distally adjoins the proximal portion of the mid tubular cylinder and the second dialysate conduit proximally adjoins the distal portion of the mid tubular cylinder; and
   wherein the first dialysate conduit and the second dialysate conduit are provided in a coaxial tube-in-tube configuration with a first outer conical reservoir conduit coaxially enclosing a first inner longitudinal tubular conduit and with a second outer conical reservoir conduit coaxially enclosing a second inner longitudinal tubular conduit, respectively;
   wherein there is provided a longitudinal distance of at least 1 mm between the inner circumferential rim and the coaxial cone disk on a longitudinal axis of the compartmentalized tubular cylinder;
   the blood compartment comprising a proximal blood chamber and a distal blood chamber;
   wherein a roof portion of the proximal blood chamber proximally adjoins a base of the first dialysate conduit;
   wherein the proximal blood chamber is connected to a blood intake tube;
   wherein a roof portion of the distal blood chamber distally adjoins a base of the second dialysate conduit;
   wherein the distal blood chamber is connected to a blood output tube; and
   wherein a proximal portion and a distal portion of the packed bundle of hollow fibers for blood flow of the blood compartment are coaxially and leakproofly connected to the proximal blood chamber and the distal blood chamber, respectively; and
   the proximal portion and the distal portion of the open central tubular column of the packed bundle of the hollow fibers are leakproofly and coaxially connected to the first inner longitudinal tubular conduit and the second inner longitudinal tubular conduit, respectively;

wherein the first dialysate conduit is configured to take a first dialysate distally through the first inner longitudinal tubular conduit in the proximal portion of the open central tubular column, and to drain the first dialysate proximally through the first outer conical reservoir conduit; and wherein the second dialysate conduit is configured to take a second dialysate proximally through the second inner longitudinal tubular conduit in the distal portion of the open central tubular column, and to drain the second dialysate distally through the second outer conical reservoir conduit.

2. The centrifugal gradient dialysate dual-chamber hemodiafiltrator according to claim 1, wherein the compartmentalized tubular cylinder further comprises:

the coaxial cone disk radially occluding the portion of the open central tubular column;

wherein the coaxial cone disk comprises an outer conical surface distally facing the distal portion of the open central tubular column; and wherein the coaxial cone disk comprises an inner conical depression proximally facing the proximal portion of the open central tubular column.

3. The centrifugal gradient dialysate dual-chamber hemodiafiltrator according to claim 2, wherein the coaxial cone disk further comprises:

wherein the coaxial cone disk radially occludes the portion of the open central tubular column so as to allow a first dialysate to flow toward the inner conical depression of the coaxial cone disk in a proximal-to-distal direction in the proximal portion of the open central tubular column;

wherein the coaxial cone disk radially occludes the portion of the open central tubular column so as to allow a second dialysate to flow toward the outer conical surface of the coaxial cone disk in a distal-to-proximal direction in the distal portion of the open central tubular column; and wherein the first dialysate flows in a coaxially opposite direction to the second dialysate.

4. The centrifugal gradient dialysate dual-chamber hemodiafiltrator according to claim 2, wherein the coaxial cone disk further comprises:

the outer conical surface distally facing toward the distal portion of the open central tubular column;

wherein the outer conical surface is configured to deflect off at a plurality of obtuse angles the second dialysate axially flowing in the distal-to-proximal direction from the distal portion of the open central tubular column to the outer conical surface of the coaxial cone disk.

5. The centrifugal gradient dialysate dual-chamber hemodiafiltrator according to claim 2, wherein the coaxial cone disk further comprises:

the inner conical depression proximally facing the proximal portion of the open central tubular column;

wherein the inner conical depression is configured to deflect off at a plurality of acute angles the first dialysate axially flowing in the proximal-to-distal direction from the proximal portion of the open central tubular column to the inner conical depression.

6. The centrifugal gradient dialysate dual-chamber hemodiafiltrator according to claim 2, wherein the coaxial cone disk further comprises:

the outer conical surface of the coaxial cone disk;

wherein the outer conical surface of the coaxial cone disk is configured deflect off a second dialysate so as to direct the second dialysate from the distal-to-proximal direction in the distal portion of the open central tubular column to the proximal-to-distal direction in the distal portion of an outer circumferential space of the mid dialysate tubular cylinder.

7. The centrifugal gradient dialysate dual-chamber hemodiafiltrator according to claim 2, wherein the coaxial cone disk further comprises:

the inner conical depression of the coaxial cone disk;

wherein the inner conical depression of the coaxial cone disk is configured to deflect off a first dialysate so as to direct a first portion of the first dialysate from the proximal-to-distal direction in the proximal portion of the open central tubular column to the distal-to-proximal direction in the proximal portion of an outer circumferential space of the mid dialysate tubular cylinder; and wherein the inner conical depression of the coaxial cone disk is configured to deflect off a first dialysate so as to direct a second portion of the first dialysate from the proximal-to-distal direction in the proximal portion of the open central tubular column to the proximal-to-distal direction in the distal portion of an outer circumferential space of the mid dialysate tubular cylinder.

8. The centrifugal gradient dialysate dual-chamber hemodiafiltrator according to claim 1, wherein the mid dialysate tubular cylinder further comprises:

the proximal portion of the mid dialysate tubular cylinder proximally opens to the first outer conical reservoir conduit through a plurality of proximal curvilinear fenestrations disposed thereof around an outer perimeter of an upper radial wall of the mid dialysate tubular cylinder, so as to flow the first dialysate from the proximal portion of the mid dialysate tubular cylinder through the plurality of the proximal curvilinear fenestrations in the distal-to-proximal direction to the first outer conical reservoir conduit.

9. The centrifugal gradient dialysate dual-chamber hemodiafiltrator according to claim 1, wherein the mid dialysate tubular cylinder further comprises:

the distal portion of the mid dialysate tubular cylinder distally opens to the second outer conical reservoir conduit through a plurality of distal curvilinear fenestrations disposed thereof around an outer perimeter of a lower radial wall of the mid dialysate tubular cylinder, so as to flow the second dialysate from the distal portion of the mid dialysate tubular cylinder through the plurality of the distal curvilinear fenestrations in the proximal-to-distal direction to the second outer conical reservoir conduit.

10. The centrifugal gradient dialysate dual-chamber hemodiafiltrator according to claim 1, wherein the mid dialysate tubular cylinder further comprises:

an outer circumferential space, provided in a cylindrically tubular configuration, disposed thereof between an outer peripheral layer of the packed bundle of the hollow fibers and the inner tubular wall of the mid dialysate tubular cylinder;

wherein the outer circumferential space is compartmentalized by the inner circumferential rim into a proximal portion of the outer circumferential space and a distal portion of the outer circumferential space;

wherein the proximal portion of the outer circumferential space proximally opens to the first outer conical reservoir through the plurality of the proximal curvilinear fenestrations;

wherein the proximal portion of the outer circumferential space is configured to transmit the first dialysate to the first outer conical reservoir conduit through the plurality of the proximal curvilinear fenestrations;
wherein the distal portion of the outer circumferential space distally opens to the second outer conical reservoir through the plurality of the distal curvilinear fenestrations; and
wherein the distal portion of the outer circumferential space is configured to transmit the second dialysate to the second outer reservoir conduit through the plurality of the distal curvilinear fenestrations.

11. The centrifugal gradient dialysate dual-chamber hemodiafiltrator according to claim 1, wherein the mid dialysate tubular cylinder further comprises:
a plurality of proximal curvilinear fenestrations circumferentially encircle the roof portion of the proximal blood chamber; and
a plurality of distal curvilinear fenestrations circumferentially encircle the roof portion of the distal blood chamber.

12. The centrifugal gradient dialysate dual-chamber hemodiafiltrator according to claim 1, wherein the proximal blood chamber further comprises:
a proximal inner coaxial tubular cylinder coaxially disposed in the proximal blood chamber;
wherein the proximal inner coaxial tubular cylinder compartmentalizes the proximal blood chamber into a proximal outer tubular columnar space outside of the proximal inner coaxial tubular cylinder and a proximal inner tubular columnar space inside the proximal inner coaxial tubular cylinder;
wherein the proximal outer tubular columnar space fixedly encases the proximal portion of the packed bundle of the hollow fibers;
wherein the proximal inner coaxial tubular cylinder proximally adjoins the first inner longitudinal tubular conduit, and is distally inserted in the proximal portion of the open central tubular column; and
wherein the proximal inner coaxial tubular cylinder is configured to distally transmit the first dialysate from the first inner longitudinal tubular conduit to the proximal portion of the open central tubular column.

13. The centrifugal gradient dialysate dual-chamber hemodiafiltrator according to claim 1, wherein the distal blood chamber further comprises:
a distal inner coaxial tubular cylinder coaxially disposed in the distal blood chamber;
wherein the distal inner coaxial tubular cylinder compartmentalizes the distal blood chamber into a distal outer tubular columnar space outside of the distal inner coaxial tubular cylinder and a distal inner tubular columnar space inside the distal inner coaxial tubular cylinder;
wherein the distal outer tubular columnar space fixedly encases the distal portion of the packed bundle of the hollow fibers;
wherein the distal inner coaxial tubular cylinder proximally adjoins the second inner longitudinal tubular conduit, and is proximally inserted in the distal portion of the open central tubular column; and
wherein the distal inner coaxial tubular cylinder is configured to proximally transmit the second dialysate from the second inner longitudinal tubular conduit to the distal portion of the open central tubular column.

14. The centrifugal gradient dialysate dual-chamber hemodiafiltrator according to claim 1, wherein the packed bundle of the hollow fibers further comprises:
an outer peripheral layer of the packed bundle of the hollow fibers;
wherein the outer peripheral layer is separated by >1 mm of a radial distance from an inner tubular wall of the mid dialysate tubular cylinder.

15. The centrifugal gradient dialysate dual-chamber hemodiafiltrator according to claim 1, wherein the packed bundle of the hollow fibers further comprises:
the open central tubular column coaxially disposed in a central portion of the packed bundle of the hollow fibers along a longitudinal axis of the packed bundle of the hollow fibers;
wherein the open central tubular column is supported by an inner string harness in a tubular configuration abuttingly disposed on a perimeter of the open central tubular column.

16. The centrifugal gradient dialysate dual-chamber hemodiafiltrator according to claim 1, wherein the packed bundle of the hollow fibers further comprises:
an inner string harness;
wherein the coaxial cone disk is fixedly and coaxially attached to a portion of the inner string harness; and
wherein the portion of the inner string harness attached to the coaxial cone disk is disposed distally to the inner circumferential rim on the longitudinal axis of the compartmentalized tubular cylinder.

17. The centrifugal gradient dialysate dual-chamber hemodiafiltrator according to claim 1, wherein the inner circumferential rim further comprises:
wherein the inner circumferential rim tightly encircles an outer peripheral layer of a portion of the packed bundle of the hollow fibers coaxially disposed inside the mid dialysate tubular cylinder, so as to partition the packed bundle of the hollow fibers into an upper half portion of and a lower half portion of the packed bundle of the hollow fibers; and
wherein the inner circumferential rim is disposed proximally to the coaxial cone disk on the longitudinal axis of the compartmentalized tubular cylinder.

18. The centrifugal gradient dialysate dual-chamber hemodiafiltrator according to claim 1, wherein the mid dialysate tubular cylinder further comprises:
a proximal portion of the second dialysate chamber, bordered proximally by the inner circumferential rim and distally by the coaxial cone disk;
wherein a longitudinal length of the proximal portion of the second dialysate chamber measures as the longitudinal distance between the coaxial cone disk and the inner circumferential rim; and
wherein the proximal portion of the second dialysate chamber is configured to simultaneously receive a portion of the first dialysate deflected off an inner conical depression and a portion of a second dialysate deflected off an outer conical surface.

* * * * *